United States Patent [19]
Malamas

[11] Patent Number: 6,110,963
[45] Date of Patent: Aug. 29, 2000

[54] ARYL-OXO-ACETIC ACIDS USEFUL IN THE TREATMENT OF INSULIN RESISTANCE AND HYPERGLYCEMIA

[75] Inventor: Michael S. Malamas, Jamison, Pa.

[73] Assignee: American Home Products Corporation, Madison, N.J.

[21] Appl. No.: 09/307,918

[22] Filed: May 10, 1999

Related U.S. Application Data

[60] Provisional application No. 60/104,591, May 12, 1998.

[51] Int. Cl.[7] .......................... A61K 31/38; A61K 31/35; A61K 31/415; C07D 333/56; C07D 417/00

[52] U.S. Cl. .......................... 514/443; 514/456; 514/394; 514/382; 514/381; 549/57; 549/58; 549/468; 548/159; 548/252

[58] Field of Search ................................. 549/57, 58, 468, 549/471, 460; 514/443, 456, 394, 381, 382; 548/159, 252

[56] References Cited

U.S. PATENT DOCUMENTS

| | | |
|---|---|---|
| 3,666,473 | 5/1972 | Colom . |
| 4,117,151 | 9/1978 | Deschamps et al. . |
| 4,133,814 | 1/1979 | Jones et al. ................... 549/57 |
| 4,808,599 | 2/1989 | Dubroeucq et al. . |
| 5,235,064 | 8/1993 | Gapinski . |
| 5,334,598 | 8/1994 | Bagley et al. . |
| 5,472,962 | 12/1995 | Koizumi et al. ................ 514/443 |
| 5,523,302 | 6/1996 | Cain et al. . |
| 5,532,382 | 7/1996 | Carlson et al. ................ 549/57 |
| 5,596,106 | 1/1997 | Cullinan et al. . |
| 5,688,821 | 11/1997 | Kees . |
| 5,698,574 | 12/1997 | Riedl et al. . |

FOREIGN PATENT DOCUMENTS

| | | |
|---|---|---|
| 0276064 | 7/1988 | European Pat. Off. . |
| 0568289 | 11/1993 | European Pat. Off. . |
| 0693491 | 1/1996 | European Pat. Off. . |
| 1249869 | 9/1967 | Germany . |
| 1291197 | 3/1969 | Germany . |
| 2616414 | 10/1977 | Germany . |
| 3110460 | 12/1982 | Germany . |
| 3342624 | 3/1984 | Germany . |
| 58-150948 | 9/1983 | Japan . |
| 60-172946 | 9/1985 | Japan . |
| 62-36661 | 2/1987 | Japan . |
| 62-36662 | 2/1987 | Japan . |
| 63-161449 | 7/1988 | Japan . |
| 3-247655 | 11/1991 | Japan . |
| 4016854 | 1/1992 | Japan . |
| 6348018 | 12/1994 | Japan . |

(List continued on next page.)

OTHER PUBLICATIONS

Ahmad, F. et al., Biochemica et Biophysica Acta, 1248, 1995, pp. 57–69.
Chang, A.Y. et al., Diabetes, 32, 1983, pp. 830–838.
Coleman, D.L., Diabetologia, 14, 1978, pp. 141–148.

(List continued on next page.)

*Primary Examiner*—Deborah C. Lambkin
*Attorney, Agent, or Firm*—Arnold S. Milowsky

[57] ABSTRACT

This invention provides compounds of Formula I having the structure

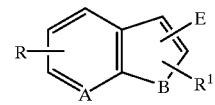

I wherein
A is C or N;
B is O, S, N, or CH=CH;
E is

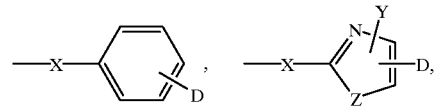

or —X—D;
D is

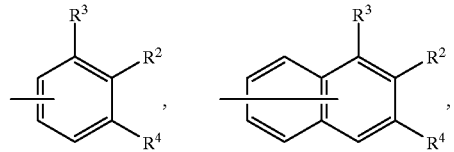

or alkyl of 1–12 carbon atoms;
X is CO, CH(OH), $CH_2$, or —CH—S-2-benzothiazole;
Y is hydrogen, alkyl of 1–6 carbon atoms, or halogen;
Z is O, S, or N;
R is hydrogen, alkyl of 1–6 carbon atoms, alkoxy of 1–6 carbon atoms, halogen, or trifluoromethyl;
$R^1$ is alkyl of 1–12 carbon atoms, aryl of 6–10 carbon atoms, aralkyl of 7–15 carbon atoms, halogen, Het-alkyl wherein the alkyl moiety contains 1–6 carbon atoms, or aryl mono-, di- or tri-substituted with a substituent selected from the group consisting of halogen, alkyl of 1–6 carbon atoms, trifluoromethyl, and alkoxy of 1–6 carbon atoms;
Het is

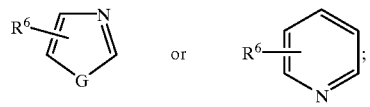

G is O, S, or N; and the remaining variables are as defined in claim 1, or a pharmaceutically acceptable salt thereof, which are useful in treating metabolic disorders related to insulin or hyperglycemia.

38 Claims, No Drawings

FOREIGN PATENT DOCUMENTS

| | | |
|---|---|---|
| 1293396 | 11/1969 | United Kingdom . |
| 9111909 | 8/1991 | WIPO . |
| 9422834 | 10/1994 | WIPO . |
| 9422835 | 10/1994 | WIPO . |
| 9608483 | 3/1996 | WIPO . |
| 9609818 | 4/1996 | WIPO . |
| 9634851 | 11/1996 | WIPO . |
| 9721693 | 6/1997 | WIPO . |

OTHER PUBLICATIONS

DeFronzo, R. A. et al., Diabetes Care, 14:3, 1991, pp. 173–194.
Goldstein, B. J., Receptor, 3, 1993, pp. 1–15.
Goldstein, B. J. et al., Mol. and Cell. Biochem., 109, 1992, pp. 107–113.
Goldstein, B. J., J. Cell. Biochem., 48, 1992, pp. 33–42.
Haring, H. U., Diabetologia, 34, 1991, pp. 848–861.
Harris, M. I. et al., Diabetes in America, 1985, Chapter 29, pp. 1–48.
Jarrett, R. J., Diabetes/Metabolism Reviews, 5:7, 1989, pp. 547–558.
Lanzetta, P. A. et al., Analytical Biochem. 100, 1979, pp. 95–97.
McGuire, M. C. et al., Diabetes, 40, Jul. 1991, pp. 939–942.
Meyerovitch, J. et al., J. Clin. Invest., 87, Apr. 1991, pp. 1286–1294.
Meyerovitch, J. et al., J. Clin. Invest., 84, Sep. 1989, pp. 976–983.
Mitsunobu, O., Synthesis Jan. 1981, pp. 1–28.
Nutaitis, C. F., Organic Preparations and Procedures Int., 23(4), 1991, pp. 403–411.
Perich, J. W. et al., Synthesis, Feb. 1988, pp. 142–144.
Phillion, D. P. et al., Tetrahedron, 27:13, 1986, pp. 1477–1480.
Pyorala, K. et al., Diabetes/Metabolism Reviews, 3:2, 1987, pp. 463–524.
Reaven, G. M. et al., Amer. J. Med., 60, 1976, pp. 80–88.
Sredy, J. et al., Metabolism, 44:8, 1995, pp. 1074–1081.
Stout, R. W., Metabolism, 34:12 (Suppl 1), Dec. 1985, pp. 7–12.
Zask, A. et al., J. Med. Chem., 33, 1990, pp. 1418–1423.
Chen, H.–M. et al., Indian J. Chem., 35B, Dec. 1996, pp. 1304–1307.
d'Ischia, M. et al., Tetrahedron, 43:2, 1987, pp. 431–434.
Dryhurst, G. et al., J. Am. Chem. Soc., 111, 1989, pp. 719–726.
Guirguis, N. R. et al., J. Prakt. Chemie, 332:3, 1990, pp. 414–418.
Guirguis, N. R. et al., Liebigs Ann. Chem., 1986, pp. 1003–1011.
Han, B. H. et al., Tetrahedron Leter, 31:8, 1990, pp. 1181–1182.
Hashem, A. I., J. Prakt. Chemie, 319:4, 1977, pp. 689–692.
Konopelski, J. P. et al., Synlett, Letters, Jul. 1996, pp. 609–611.
Kuroda, T. et al., J. Org. Chem., 59, 1994, pp. 7353–7357.
Kuroda, T. et al., J. Chem. Soc., Chem. Commun., 1991, pp. 1635–1636.
Lefker, B. A. et al., Tetrahedron Letters, 35:29, 1994, pp. 5205–5208.
Molina, P. et al., Tetrahedron, 50:17, 1994, pp. 5027–5036.
Molina, P. et al., Tetrahedron Letters, 34:17, 1993, pp. 2809–2812.
Napolitano, A. et al., Tetrahedron, 45:21, 1989, pp. 6749–6760.
Schuster, I. I., et al., J. Org. Chem., 53, 1988, pp. 5819–5825.
Buu–Hoi, N. P. et al., J. Chem. Soc., 1957, pp. 625–628.
Brown, E. V. et al., J. Med. Chem., 14:1, 1971, pp. 84–85.
Kimura, T. et al., Tetrahedron Letters, 36:7, 1995, pp. 1079–1080.
Schuster, I. I. et al., J. Org. Chem. 53, 1988, pp. 5819–5825.
Han, B. H. et al., Tetrahedron Letters, 31:8, 1990, pp. 1181–1182.
Mitsunobu, O., Synthesis, Jan. 1981, pp. 1–28.
Kano, S. et al., Heterocycles, 19:6, 1982, pp. 1033–1037.
Martin, S.F. et al., J. Org. Chem., 49, 1984, pp. 2512–2513.
Eckert, T. et al., Arch. Pharm., 315, 1982, pp. 569–570.
Goldenberg, C. et al., Eur. J. Med. Chem., Chim. Ther., 12:1, Jan.–Feb. 1977, pp. 81–86.
Artini, D. et al., Arzneim.–Forsch. (Drug Res.), 21:1, 1971, pp. 30–36.
Ayyangar, N.R. et al., Synthesis, Apr. 1991, pp. 322–324.
Darchen, A. et al., J.C.S. Chem. Comm., 1976, p. 820.
De Cointet, P. et al., Chimie Therapeutique, 5, Sep.–Oct. 1973, pp. 574–587.
Massolini, G. et al., II Farmaco, 45(2), 1990, pp. 263–268.
Miyaura, N. et al., Synthetic Communications, 11:7, 1951, pp. 513–519.
Barraclough, P. et al., Arch. Pharm., 323, 1990, pp. 507–512.
Liebeskind, L. S. et al., J. Org. Chem., 55, 1990, pp. 5359–5364.
Toth, I., Liebigs Ann. Chem., 1994, pp. 685–688.

ARYL-OXO-ACETIC ACIDS USEFUL IN THE TREATMENT OF INSULIN RESISTANCE AND HYPERGLYCEMIA

This application claims the benefit of U.S. provisional application Ser. No. 60/104,591, which was converted from U.S. patent application Ser. No. 09/076,420, filed May 12, 1998, pursuant to a petition filed under 37 C.F.R. 1.53(c)(2)(i) on Jun. 16, 1998.

BACKGROUND OF THE INVENTION

The prevalence of insulin resistance in glucose intolerant subjects has long been recognized. Reaven et al (*American Journal of Medicine* 1976, 60, 80) used a continuous infusion of glucose and insulin (insulin/glucose clamp technique) and oral glucose tolerance tests to demonstrate that insulin resistance existed in a diverse group of nonobese, nonketotic subjects. These subjects ranged from borderline glucose tolerant to overt, fasting hyperglycemia. The diabetic groups in these studies included both insulin dependent (IDDM) and noninsulin dependent (NIDDM) subjects.

Coincident with sustained insulin resistance is the more easily determined hyperinsulinemia, which can be measured by accurate determination of circulating plasma insulin concentration in the plasma of subjects. Hyperinsulinemia can be present as a result of insulin resistance, such as is in obese and/or diabetic (NIDDM) subjects and/or glucose intolerant subjects, or in IDDM subjects, as a consequence of over injection of insulin compared with normal physiological release of the hormone by the endocrine pancreas.

The association of hyperinsulinemia with obesity and with ischemic diseases of the large blood vessels (e.g. atherosclerosis) has been well established by numerous experimental, clinical and epidemiological studies (summarized by Stout, *Metabolism* 1985, 34, 7, and in more detail by Pyorala et al, *Diabetes/Metabolism Reviews* 1987, 3, 463). Statistically significant plasma insulin elevations at 1 and 2 hours after oral glucose load correlates with an increased risk of coronary heart disease.

Since most of these studies actually excluded diabetic subjects, data relating the risk of atherosclerotic diseases to the diabetic condition are not as numerous, but point in the same direction as for nondiabetic subjects (Pyorala et al). However, the incidence of atherosclerotic diseases in morbidity and mortality statistics in the diabetic population exceeds that of the nondiabetic population (Pyorala et al; Jarrett *Diabetes/Metabolism Reviews* 1989,5, 547; Harris et al, Mortality from diabetes, in *Diabetes in America* 1985).

The independent risk factors obesity and hypertension for atherosclerotic diseases are also associated with insulin resistance. Using a combination of insulin/glucose clamps, tracer glucose infusion and indirect calorimetry, it has been demonstrated that the insulin resistance of essential hypertension is located in peripheral tissues (principally muscle) and correlates directly with the severity of hypertension (DeFronzo and Ferrannini, *Diabetes Care* 1991, 14, 173). In hypertension of the obese, insulin resistance generates hyperinsulinemia, which is recruited as a mechanism to limit further weight gain via thermogenesis, but insulin also increases renal sodium reabsorption and stimulates the sympathetic nervous system in kidneys, heart, and vasculature, creating hypertension.

It is now appreciated that insulin resistance is usually the result of a defect in the insulin receptor signaling system, at a site post binding of insulin to the receptor. Accumulated scientific evidence demonstrating insulin resistance in the major tissues which respond to insulin (muscle, liver, adipose), strongly suggests that a defect in insulin signal transduction resides at an early step in this cascade, specifically at the insulin receptor kinase activity, which appears to be diminished (reviewed by Haring, *Diabetalogia* 1991, 34, 848).

Protein-tyrosine phosphatases (PTPases) play an important role in the regulation of phosphorylation of proteins. The interaction of insulin with its receptor leads to phosphorylation of certain tyrosine molecules within the receptor protein, thus activating the receptor kinase. PTPases dephosphorylate the activated insulin receptor, attenuating the tyrosine kinase activity. PTPases can also modulate post-receptor signaling by catalyzing the dephosphorylation of cellular substrates of the insulin receptor kinase. The enzymes that appear most likely to closely associate with the insulin receptor and therefore, most likely to regulate the insulin receptor kinase activity, include PTP1B, LAR, PTPα and SH-PTP2 (B. J. Goldstein, *J. Cellular Biochemistry* 1992, 48, 33; B. J. Goldstein, *Receptor* 1993, 3, 1–15,; F. Ahmad and B. J. Goldstein *Biochim. Biophys Acta* 1995, 1248, 57–69).

McGuire et al. (*Diabetes* 1991, 40, 939), demonstrated that nondiabetic glucose intolerant subjects possessed significantly elevated levels of PTPase activity in muscle tissue vs. normal subjects, and that insulin infusion failed to suppress PTPase activity as it did in insulin sensitive subjects.

Meyerovitch et al (*J. Clinical Invest.* 1989, 84, 976) observed significantly increased PTPase activity in the livers of two rodent models of IDDM, the genetically diabetic BB rat, and the STZ-induced diabetic rat. Sredy et al (*Metabolism,* 44, 1074, 1995) observed similar increased PTPase activity in the livers of obese, diabetic ob/ob mice, a genetic rodent model of NIDDM.

The compounds of this invention have been shown to inhibit PTPases derived from rat liver microsomes and human-derived recombinant PTPase-1B (hPTP-1B) in vitro. They are useful in the treatment of insulin resistance associated with obesity, glucose intolerance, diabetes mellitus, hypertension and ischemic diseases of the large and small blood vessels.

DESCRIPTION OF THE INVENTION

This invention provides a compound of formula I having the structure

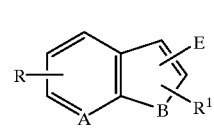

wherein
A is C or N;
B is O, S, N, or CH=CH;
E is

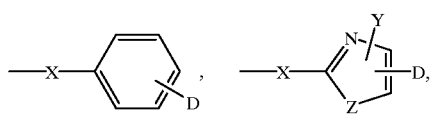

or —X—D;
D is

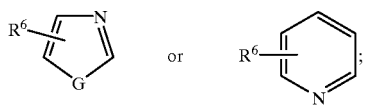

or alkyl of 1–12 carbon atoms;
X is CO, CH(OH), CH$_2$, or —CH—S-2-benzothiazole;
Y is hydrogen, alkyl of 1-6 carbon atoms, or halogen;
Z is O, S, or N;
R is hydrogen, nitro, alkyl of 1–6 carbon atoms, alkoxy of 1–6 carbon atoms, halogen, or trifluoromethyl;
R$^1$ is alkyl of 1–12 carbon atoms, aryl of 6–10 carbon atoms, aralkyl of 7–15 carbon atoms, halogen, Het-alkyl wherein the alkyl moiety contains 1–6 carbon atoms, or aryl mono-, di- or tri-substituted with a substituent selected from the group consisting of halogen, alkyl of 1-6 carbon atoms, trifluoromethyl, and alkoxy of 1–6 carbon atoms;
Het is

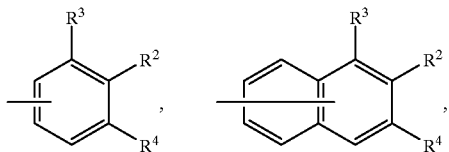

G is O, S, or N;
R$^2$ is hydrogen, halogen, alkyl of 1–6 carbon atoms, or —OR$^5$
R$^3$ and R$^4$ are each, independently, hydrogen, halogen, alkyl of 1–8 carbon atoms, aryl of 6–12 carbon atoms, nitro, amino, alkylsulfonamide, alkylsulfonamide, cycloalkyl of 3–8 carbon atoms, heterocycle of 5 to 7 ring atom containing from 1 to 3 heteroatoms selected from oxygen, nitrogen, or sulfur, or aryl of 6–10 carbon atoms mono-, di- or tri-substituted with a substituent selected from the group consisting of halogen, alkyl of 1–6 carbon atoms, trifluoromethyl, alkoxy of 1–6 carbon atoms;
R$^5$ is hydrogen, alkyl of 1–6 carbon atoms, —CH(R$^7$)R$^8$, —C(CH$_2$)$_n$CO$_2$R$^9$, —C(CH$_3$)$_2$CO$_2$R$^9$, CH(R$^7$)(CH$_2$)$_n$CO$_2$R$^9$, or —CH(R$^7$)C$_6$H$_4$CO$_2$R$^9$;
R$^6$ is alkylene of 1–3 carbon atoms;
R$^7$ is hydrogen, alkyl of 1–6 carbon atoms, aryl of 6–12 carbon atoms, aralkyl of 6–12 carbon atoms, cycloalkyl of 3–8 carbon atoms, phthalic acid, or Q-alkyl wherein the alkyl moiety contains 1–6 carbon atoms;
Q is

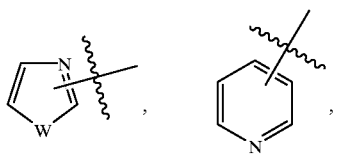

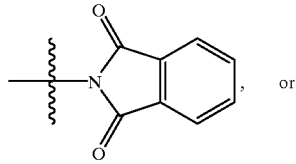

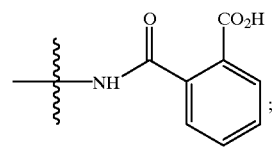

R$^8$ is —CO$_2$R$^{11}$, —CONHR$^{11}$, tetrazole, or —PO$_3$R$^{11}$;
R$^9$ is hydrogen, alkyl of 1–6 carbon atoms, aryl of 6–12 carbon atoms, or aralkyl of 7–15 carbon atoms;
W is O, N, or S;
R$^{11}$ is hydrogen, alkyl of 1–6 carbon atoms, aryl of 6–12 carbon atoms, or aralkyl of 7–15 carbon atoms;
n=1–6;

or a pharmaceutically acceptable salt thereof, which are useful in treating metabolic disorders related to insulin resistance or hyperglycemia.

Pharmaceutically acceptable salts can be formed from organic and inorganic acids, for example, acetic, propionic, lactic, citric, tartaric, succinic, fumaric, maleic, malonic, mandelic, malic, phthalic, hydrochloric, hydrobromic, phosphoric, nitric, sulfuric, methanesulfonic, napthalenesulfonic, benzenesulfonic, toluenesulfonic, camphorsulfonic, and similarly known acceptable acids when a compound of this invention contains a basic moiety. Salts may also be formed from organic and inorganic bases, preferably alkali metal salts, for example, sodium, lithium, or potassium, when a compound of this invention contains a carboxylate or phenolic moiety, or similar moiety capable of forming base addition salts.

Alkyl includes both straight chain as well as branched moieties. Halogen means bromine, chlorine, fluorine, and iodine. It is preferred that the aryl portion of the aryl or aralkyl substituent is a phenyl, naphthyl or 1,4-benzodioxan-5-yl group; with phenyl being most preferred. The aryl moiety may be optionally mono-, di-, or tri- substituted with a substituent selected from the group consisting of alkyl of 1–6 carbon atoms, alkoxy of 1–6 carbon atoms, trifluoromethyl, halogen, alkoxycarbonyl of 2–7 carbon atoms, alkylamino of 1–6 carbon atoms, and dialkylamino in which each of the alkyl groups is of 1–6 carbon atoms, nitro, cyano, —CO$_2$H, alkylcarbonyloxy of 2–7 carbon atoms, and alkylcarbonyl of 2–7 carbon atoms.

The compounds of this invention may contain an asymmetric carbon atom and some of the compounds of this invention may contain one or more asymmetric centers and may thus give rise to optical isomers and diastereomers. While shown without respect to stereochemistry in Formula I, the present invention includes such optical isomers and diastereomers; as well as the racemic and resolved, enantiomerically pure R and S stereoisomers; as well as other mixtures of the R and S stereoisomers and pharmaceutically acceptable salts thereof.

Preferred compounds of this invention are those compounds of Formula I, in which:
A is C;
R is hydrogen;
$R^1$ is hydrogen, alkyl of 1–6 carbon atoms, or aralkyl of 7–15 carbon atoms; and
$R^3$ and $R^4$ are each, independently, hydrogen or halogen;
or a pharmaceutically acceptable salt thereof
Specifically preferred compounds of the present invention are set forth below:
6-[(2-butyl-benzofuran-3-yl)-hydroxy-methyl-naphthalen-2-ol
6-[(2-butyl-benzofuran-3-ylmethyl)-naphthalen-2-ol
1-bromo-6-(2-butyl-benzofuran-3-ylmethyl)-naphthalen-2-ol
[1-bromo-6-(2-butyl-benzofuran-3-ylmethyl)-naphthalen-2-yloxy]-acetic acid
2-[1-bromo-6-(2-butyl-benzofuran-3-ylmethyl)-naphthalen-2-yloxy]-3-phenyl-propionic acid
5-[1-bromo-6-(2-butyl-benzofuran-3-ylmethyl)-naphthalen-2-yloxymethyl]-1H-tetrazole
6-(2-butyl-benzofuran-3-ylmethyl)-1-iodo-naphthalen-2-ol
2-[-6-(2-butyl-benzofuran-3-ylmethyl)-1-iodo-naphthalen-2-yloxy]-3-phenyl-propionic acid
1-bromo-6-[(2-butyl-benzofuran-3-yl)-hydroxy-methyl]-naphthalen-2-ol
[1-bromo-6-(2-butyl-benzofuran-3-carbonyl)-naphthalen-2-yloxy]-acetic acid
2-[1-bromo-6-(2-butyl-benzofuran-3-carbonyl)-naphthalen-2-yloxy]-3-phenyl-propionic acid
[5-bromo-6-(1H-tetrazol-5-ylmethoxy)-naphthalen-2-yl]-(2-butyl-benzofuran-3-yl)methanone
6-(2-benzyl-benzo[b]thiophen-3-ylmethyl)-1-bromo-naphthalen-2-ol
4'-[(2-butyl-benzofuran-3-yl)-hydroxy-methyl]-biphenyl-4-ol
(2-butyl-benzofuran-3-yl)-(4'-hydroxy-biphenyl-4-yl)-methanone
4'-[(2-butyl-benzofuran-3-ylmethyl]-biphenyl-4-ol
[4'-[(2-butyl-benzofuran-3-ylmethyl]-biphenyl-4-yloxy]-acetic acid
5-[4'-(2-butyl-benzofuran-3-ylmethyl)-biphenyl-4-yloxymethyl]-1H-tetrazole
{4'-[(2-butyl-benzofuran-3-yl)-hydroxy-methyl]-biphenyl-4-yloxy}-acetic acid
3,5-dibromo-4'-[(2-butyl-benzofuran-3-yl)-hydroxy-methyl]-biphenyl-4-ol
4'-[(2-benzyl-benzo[b]thiophen-3-yl)-hydroxy-methyl]-biphenyl-4-ol
(2-butyl-benzofuran-3-yl)-[5-(4-methoxy-phenyl)-oxazol-2-yl]-methanol
(2-butyl-benzofuran-3-yl)-[5-(4-methoxy-phenyl)-oxazol-2-yl]-methanone
2-(2-butyl-benzofuran-3-ymethyl)-5-(4-methoxy-phenyl)-oxazole
[4-bromo-5-(4-methoxy-phenyl)-oxazol-2-yl]-(2-butyl-benzofuran-3-yl)-methanone
4-bromo-5-(6-bromo-2-butyl-benzofaran-3-ylmethyl)-5-(4-methoxy-phenyl)-oxazole
6-[(benzothiazol-2-ylsulfanyl)-(2-butyl-benzofaran-3-yl)-methyl]-naphthalen-2-ol
4'-[(2-butyl-benzofuran-3-yl)-(benzothiazol-2-ylsulfanyl)-methyl]-biphenyl-4-ol
2-[1-(benzo[b]thiophen-2-yl)-octylsulfanyl]-benzothiazole
2-[(4-bromo-phenyl)-(2-butyl-benzofuran-3-yl)-methylsulfanyl]-benzothiazole
2-[(4-bromo-naphthalen-1-yl)-(2-butyl-benzofuran-3-yl)-methylsulfanyl]-benzothiazole
2-[(2-butyl-benzofuran-3-yl)-phenyl-methylsulfanyl]-benzothiazole
[2,6-dibromo-4-(naphthalene-2-carbonyl)-phenoxy]-acetic acid
5-[2,6-dibromo-4-(naphthalen-2-ylmethyl)-phenoxymethyl]-1H-tetrazole
or a pharmaceutically acceptable salt thereof.

The compounds of this invention were be prepared according to the following schemes from commercially available starting materials or starting materials which can be prepared using to literature procedures. These schemes show the preparation of representative compounds of this invention.

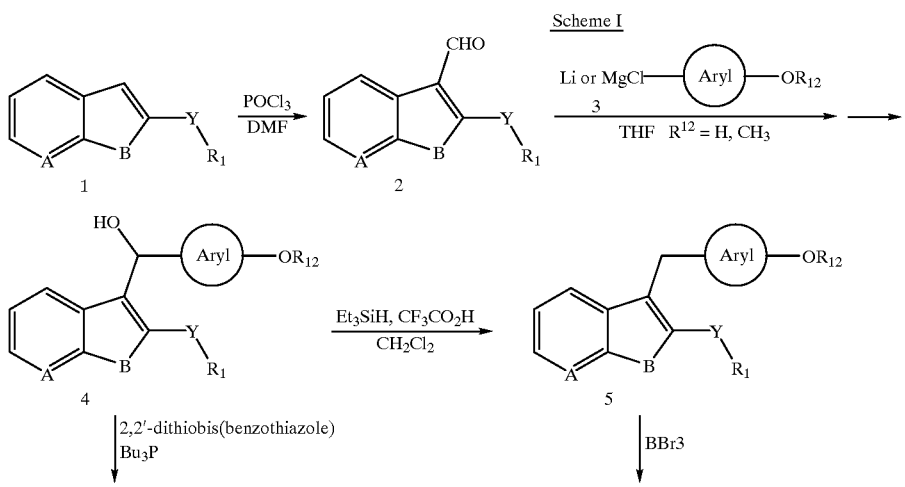

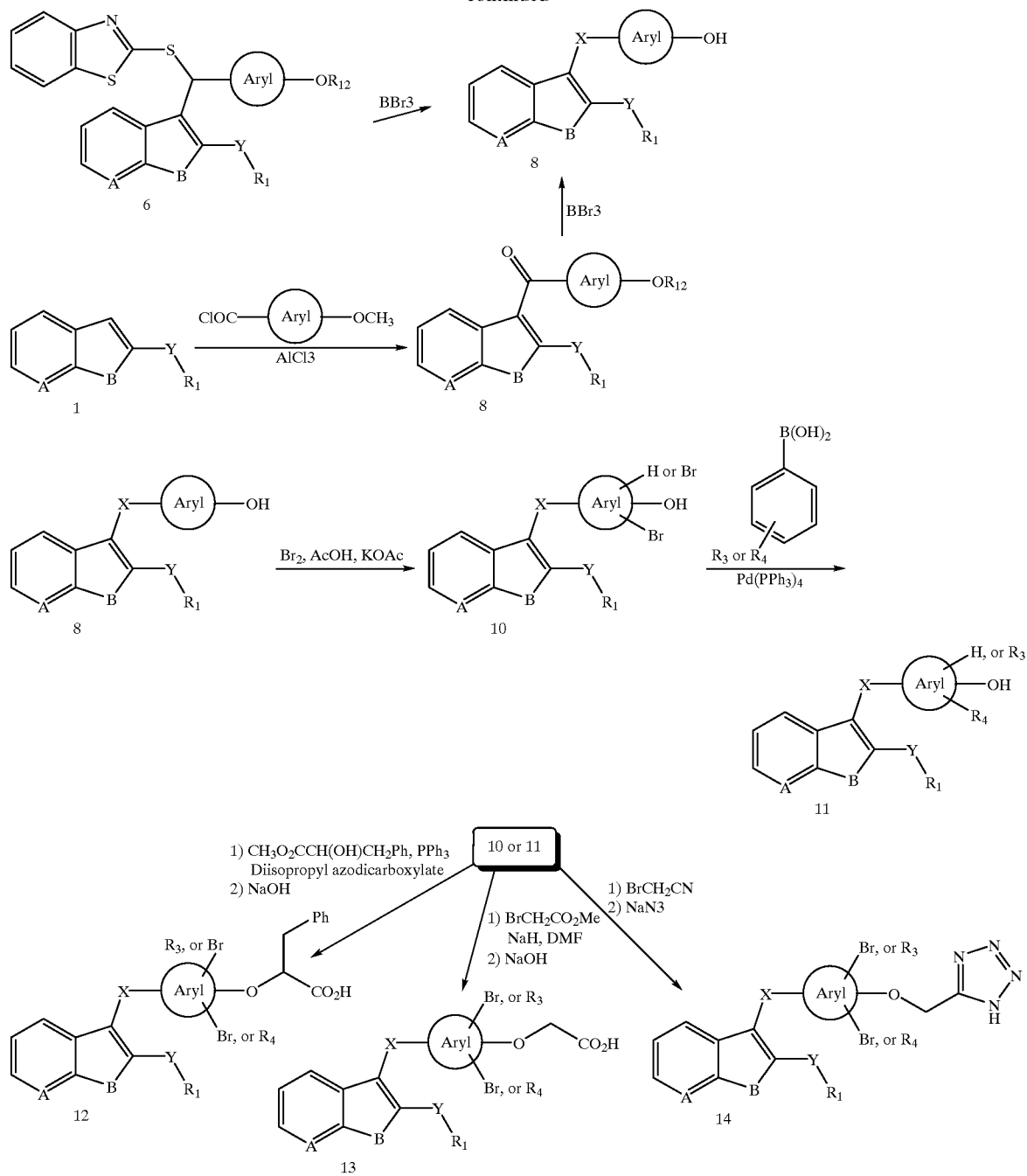

In Scheme I compounds (1) that are either commercially available or can be prepared by known methodologies from the 2-lithiated derivatives, obtained by treatment with alkyllithium reagents, of compounds (1) and the appropriate electrophiles Y—$R^1$ [ref. Org. React. 1979, volue 26]. Compounds (1) can be converted to 3-carboxaldehydes (2) upon treatment with phosphorus oxychloride and N,N-dimethylformamide [ref. Chim. Ther. 1996, 4, 221–227]. Aldehydes (2) can be treated with aromatic or heteroaromatic lithium (prepared by lithium halogen exchange, using for example n-BuLi) or Grignard reagents (3) to afford methyl-alcohols (4). Alcohols (4) can be reduced with triethylsilane/trifluoroacetic acid to produce (5) or can be converted to benzothiazoles (6) upon reaction with 2,2'-dithiobis(benzothiazole) and tributylphosphine. Compounds (1) can also be converted to ketones (7) upon treatment with acyl chlorides and aluminum chloride [Friedel-Crafts and Related Reactions, Wiley Interscience, New York, 1963–1965]. Compounds (5), (6), and (7) can produce phenols (8) upon treatment with boron tribromide. Compounds (8) can be monobrominated or dibrominated (10) with bromine in the presence of potassium acetate and acetic acid. The brominated compounds (10) can be converted to terphenyl analogs (11) using the Suzuki protocol (arylboronic acids / palladium catalyst) [ref. Syn. Comm. 1981, 11, 513–519]. Compounds (10) and (11) can be treated with bromoacetonitrile in the presence of sodium hydride to give oxo-nitriles that can subsequently be converted to tetrazoles (14) upon treatment with sodium azide and ammonium chloride. Secondly, compounds (10) and (11) can be converted to the oxoacetic acids (13) upon treatment with methyl bromoacetate, followed by saponification with sodium hydroxide. Thirdly, compounds (10) and (11) can be converted to carboxylic acids (12) by using the Mitsunobu protocol [ref. *Synthesis.* 1981, 1–27], for example, phenyl-lactic acid methyl ester, triphenylphosphine and diisopropyl azodicarboxylate. Conversion of either (10) or (11) to (12), (13) or (14) when X is —CH(OH)— will require the masking of the hydroxyl group, for examle with a silyl reagent, followed by unmasking at the last step, for example with tetrabutylammonium fluoride.

The compounds of this invention are useful in treating metabolic disorders related to insulin resistance or hyperglycemia, typically associated with obesity or glucose intolerance. The compounds of this invention are therefore, particularly useful in the treatment or inhibition of type II diabetes. The compounds of this invention are also useful in modulating glucose levels in disorders such as type I diabetes.

The ability of compounds of this invention to treat or inhibit disorders related to insulin resistance or hyperglycemia was established with representative compounds of this invention in the following two standard pharmacological test procedures which measure the inhibition of PTPase.

Inhibition of tri-phosphorylated insulin receptor dodeca-phosphopeptide dephosphorylation by rat hepatic protein-tyrosine phosphatases (PTPases)

This standard pharmacological test procedure assess the inhibition of rat hepatic microsomal PTPase activity using, as substrate, the phosphotyrosyl dodecapeptide corresponding to the 1142–1153 insulin receptor kinase domain, phosphorylated on the 1146, 1150 and 1151 tyrosine residues. The procedure used and results obtained are briefly outlined below.

Preparation of Microsomal Fraction:

Rats (Male Sprague-Dawley rats (Charles River, Kingston, N.Y.) weighing 100–150 g, maintained on standard rodent chow (Purina)) are sacrificed by asphyxiation with CO2 and bilateral thoracotomy. The liver is removed and washed in cold 0.85% (w/v) saline and weighed. The tissue is homogenized on ice in 10 volumes of Buffer A and the microsomes are isolated essentially as described by Meyerovitch J, Rothenberg P, Shechter Y, Bonner-Weir S, Kahn C R. Vanadate normalizes hyperglycemia in two mouse models of non-insulin-dependent diabetes mellitus. *J Clin Invest* 1991; 87:1286–1294 and Alberts B, Bray D, Lewis J, Raff M, Roberts K, Watson J D, editors. Molecular biology of the cell. New York: Garland Publishing, Inc., 1989 with minor modifications. The liver homogenate is filtered through silk to remove any remaining tissue debris and then is centrifuged at 10,000×g for 20 minutes at 40 C. The supernatant is decanted and centrifuged at 100,000×g for 60 minutes at 40 C. The pellet, microsomes and small vesicles, is resuspended and lightly homogenized in: 20 mM TRIS-HCl (pH 7.4), 50 mM 2-mercaptoethanol, 250 mM sucrose, 2 mM EDTA, 10 mM EGTA, 2 mM AEBSF, 0.1 mM TLCK, 0.1 mM TPCK, 0.5 mM benzamidine, 25 ug/ml leupeptin, 5 ug/ml pepstatin A, 5 ug/mil;H5B antipain, 5 ug/ml chymostatin, 10 ug/ml aprotinin (Buffer A), to a final concentration of approximately 850 ug protein/mil. Protein concentration is determined by the Pierce Coomassie Plus Protein Assay using crystalline bovine serum albumin as a standard (Pierce Chemical Co., Rockford, Ill.).

Measurement of PTPase activity:

The malachite green-ammonium molybdate method, as described by Lanzetta P A, Alvarez L J, Reinach P S, Candia O A was used. An improved assay for nanomolar amounts of inorganic phosphate. *Anal. Biochem.* 1979;100:95–97, and adapted for the platereader, is used for the nanomolar detection of liberated phosphate by rat hepatic microsomal PTPases. The test procedure uses, as substrate, a dodeca-phosphopeptide custom synthesized by AnaSpec, Inc. (San Jose, Calif.). The peptide, TRDIYETDYYRK, corresponding to the 1142–1153 catalytic domain of the insulin receptor, is tyrosine phosphorylated on the 1146, 1150 and 1151 tyrosine residues. The microsomal fraction (83.25 ul) is preincubated for 10 min at 37 deg. C with or without test compound (6.25 ul) and 305.5 ul of the 81.83 mM HEPES reaction buffer, pH 7.4. Peptide substrate, 10.5 ul at a final concentration of 50 uM, is equilibrated to 37 deg. C. in a LABLINE Multi-Blok heater equipped with a titerplate adapter. The preincubated microsomal preparation (39.5 ul) with or without drug is added to initiate the dephosphorylation reaction, which proceeds at 37 deg. C. for 30 min. The reaction is terminated by the addition of 200 ul of the malachite green-ammonium molybdate-Tween 20 stopping reagent (MG/AM/Tw). The stopping reagent consists of 3 parts 0.45% malachite green hydrochloride, 1 part 4.2% ammonium molybdate tetrahydrate in 4 N HCl and 0.5% Tween 20. Sample blanks are prepared by the addition of 200 ul MG/AM/Tw to substrate and followed by 39.5 ul of the preincubated membrane with or without drug. The color is allowed to develop at room temperature for 30 min and the sample absorbances are determined at 650 nm using a platereader (Molecular Devices). Samples and blanks are prepared in quadruplicates. Screening activity of 50 uM (final) drug is accessed for inhibition of microsomal PTPases.

Calculations:

PTPase activities, based on a potassium phosphate standard curve, are expressed as nmoles of phosphate released/min/mg protein. Test compound PTPase inhibition is calculated as percent of control. A four parameter non-linear logistic regression of PTPase activities using SAS release 6.08, PROC NLIN, is used for determining IC50 values of test compounds. All compounds were administered at a concentration of 50 $\mu$M. The following results were obtained using representative compounds of this invention.

| Example | % Change from Control |
|---|---|
| 1 | −31 |
| 2 | −37 |
| 3 | −37 |
| 4 | −65 |
| 5 | −59 |
| 6 | −62 |
| 7 | −24 |
| 8 | −58 |
| 10 | −69 |
| 11 | −77 |
| 12 | −70 |
| 13 | −37 |
| 15 | −20 |
| 16 | −28 |
| 17 | −76 |
| 18 | −65 |
| 19 | −24 |
| 20 | −22 |
| 22 | −38 |
| 29 | −24 |
| phenylarsine (Reference) | −57 |

Inhibition of Tri-Phosphorylated Insulin Receptor Dodecaphosphopeptide Dephosphorylation by hPTP1B This standard pharmacological test procedure assess the inhibition of recombinant rat protein tyrosine phosphatase, PTP1B, activity using, as substrate, the phosphotyrosyl dodecapeptide corresponding to the 1142–1153 insulin receptor kinase domain, phosphorylated on the 1146, 1150 and 1151 tyrosine residues. The procedure used and results obtained are briefly described below.

Human recombinant PTP1B was prepared as described by Goldstein (see Goldstein et al. *Mol. Cell. Biochem.* 109, 107, 1992). The enzyme preparation used was in microtubes containing 500–700 μg/ml protein in 33 mM Tris-HCl, 2 mM EDTA, 10% glycerol and 10 mM 2-mercaptoethanol.
Measurement of PTPase activity:

The malachite green-ammonium molybdate method, as described (Lanzetta et al. *Anal. Biochem.* 100, 95, 1979) and adapted for a platereader, is used for the nanomolar detection of liberated phosphate by recombinant PTP1B. The test procedure uses, as substrate, a dodecaphosphopeptide custom synthesized by AnaSpec, Inc. (San Jose, Calif.). the peptide, TRDIYETDYYRK, corresponding to the 1142–1153 catalytic domain of the insulin receptor, is tyrosine phosphorylated on the 1146, 1150, and 1151 tyrosine residues. The recombinant rPTP1B is diluted with buffer (pH 7.4, containing 33 mM Tris-HCl, 2 mM EDTA and 50 mM b-mercaptoethanol) to obtain an approximate activity of 1000–2000 nmoles/min/mg protein. The diluted enzyme (83.25 mL) is preincubated for 10 min at 37° C. with or without test compound (6.25 mL) and 305.5 mL of the 81.83 mM HEPES reaction buffer, pH 7.4 peptide substrate, 10.5 ml at a final concentration of 50 mM, and is equilibrated to 37° C. in a LABLINE Multi-Blok heater equipped with a titerplate adapter. The preincubated recombinant enzyme preparation (39.5 ml) with or without drug is added to initiate the dephosphorylation reaction, which proceeds at 37° C. for 30 min. The reaction is terminated by the addition of 200 mL of the malachite green-ammonium molybdate-Tween 20 stopping reagent (MG/AM/Tw). The stopping reagent consists of 3 parts 0.45% malachite green hydrochloride, 1 part 4.2% ammonium molybdate tetrahydrate in 4 N HCl and 0.5% Tween 20. Sample blanks are prepared by the addition of 200 mL MG/AM/Tw to substrate and followed by 39.5 ml of the preincubated recombinant enzyme with or without drug. The color is allowed to develop at room temperature for 30 min. and the sample absorbances are determined at 650 nm using a platereader (Molecular Devices). Sample and blanks are prepared in quadruplicates.
Calculations:

PTPase activities, based on a potassium phosphate standard curve, are expressed as nmoles of phosphate released/min/mg protein. Inhibition of recombinant PTP1B by test compounds is calculated as percent of phosphatase control. A four parameter non-linear logistic regression of PTPase activities using SAS release 6.08, PROC NLIN, is used for determining $IC_{50}$ values of test compounds. The following results were obtained.

| Example | IC50 (μM) |
| --- | --- |
| 1 | 1.16 |
| 2 | 1.35 |
| 3 | 0.33 |
| 4 | 1.44 |
| 5 | 0.37 |
| 6 | 0.7 |
| 7 | 0.31 |
| 8 | 0.31 |
| 9 | 0.48 |
| 10 | −46 (2.5 uM) |
| 11 | 1.23 |
| 12 | 1.13 |
| 13 | 1.04 |
| 14 | 0.23 |
| 15 | −53 (2.5 uM) |
| 16 | 1.19 |
| 17 | 1.15 |
| 18 | 0.51 |
| 19 | 0.54 |
| 20 | 1.4 |
| 21 | −36 (2.5) |
| 23 | −55 (2.5 uM) |
| 24 | −35 (2.5 uM) |
| 25 | 1.36 |
| 26 | 1.24 |
| 27 | 1.0 |
| 28 | 1.16 |
| 29 | 1.86 |
| 30 | 0.58 |
| 31 | 0.59 |
| 32 | 1.0 |
| Phenylarsine oxide (reference standard) | 39.7 |
| Sodium orthovanadate (reference standard) | 244.8 |
| Ammonium molybdate tetrahydrate (reference standard) | 8.7 |

The blood glucose lowering activity of representative compounds of this invention were demonstrated in an in vivo standard procedure using diabetic (ob/ob) mice. The procedures used and results obtained are briefly described below.

The non-insulin dependent diabetic (NIDDM) syndrome can be typically characterizes by obesity, hyperglycemia, abnormal insulin secretion, hyperinsulinemia and insulin resistance. The genetically obese-hyperglycemic ob/ob mouse exhibits many of these metabolic abnormalities and is thought to be a useful model to search for hypoglycemic agents to treat NIDDM [Coleman, D.: Diabetologia 14: 141–148, 1978].

In each test procedure, mice [Male or female ob/ob (C57 B1/6J) and their lean litermates (ob/+ or +/+, Jackson Laboratories) ages 2 to 5 months (10 to 65 g)] of a similar age were randomized according to body weight into 4 groups of 10 mice. The mice were housed 5 per cage and are maintained on normal rodent chow with water ad libitum. Mice received test compound daily by gavage (suspended in 0.5 ml of 0.5% methyl cellulose); dissolved in the drinking water; or admixed in the diet. The dose of compounds given ranges from 2.5 to 200 mg/kg body weight/day. The dose is calculated based on the fed weekly body weight and is expressed as active moiety. The positive control, ciglitazone (5-(4-(1-methylcyclohexylmethoxy)benzyl)-2,4-dione, see Chang, A., Wyse, B., Gilchrist, B., Peterson, T. and Diani, A. Diabetes 32: 830–838, 1983.) was given at a dose of 100 mg/kg/day, which produces a significant lowering in plasma glucose. Control mice received vehicle only.

On the morning of Day 4, 7 or 14 two drops of blood (approximetly 50 ul) were collected into sodium fluoride containing tubes either from the tail vein or after decapitation. For those studies in which the compound was administered daily by gavage the blood samples were collected two hours after compound administration. The plasma was isolated by centrifugation and the concentration of glucose is measured enzymatically on an Abbott V. P. Analyzer.

For each mouse, the percentage change in plasma glucose on Day 4, 7 or 14 is calculated relative to the mean plasma glucose of the vehicle treated mice. Analysis of variance followed by Dunett's Comparison Test (one-tailed) are used to estimate the significant difference between the plasma glucose values from the control group and the individual compound treated groups (CMS SAS Release 5.18).

The results shown in the table below shows that the compounds of this invention are antihyperglycemic agents as they lower blood glucose levels in diabetic mice.

| Example | Dose (mg/Kg) | % Change Glucose from Vehicle | % Change Insulin from Vehicle |
|---|---|---|---|
| 5 | 100 | −25.6 | −37a |
| 8 | 100 | −11 | −33 |
| 9 | 100 | −6a | −38 |
| 12 | 100 | −24.8 | 12a |
| 34 | 100 | −27.8 | −18 |
| Ciglitazone (reference standard | 100 | −43 | −39 | a - no significant activity (p < 0.05) at this dose.

Based on the results obtained in the standard pharmacological test procedures, representative compounds of this invention have been shown to inhibit PTPase activity and lower blood glucose levels in diabetic mice, and are therefore useful in treating metabolic disorders related to insulin resistance or hyperglycemia, typically associated with obesity or glucose intolerance. More particularly, the compounds of this invention useful in the treatment or inhibition of type II diabetes, and in modulating glucose levels in disorders such as type I diabetes. As used herein, the term modulating means maintaining glucose levels within clinically normal ranges.

Effective administration of these compounds may be given at a daily dosage of from about 1 mg/kg to about 250 mg/kg, and may given in a single dose or in two or more divided doses. Such doses may be administered in any manner useful in directing the active compounds herein to the recipient's bloodstream, including orally, via implants, parenterally (including intravenous, intraperitoneal and subcutaneous injections), rectally, vaginally, and transdermally. For the purposes of this disclosure, transdermal administrations are understood to include all administrations across the surface of the body and the inner linings of bodily passages including epithelial and mucosal tissues. Such administrations may be carried out using the present compounds, or pharmaceutically acceptable salts thereof, in lotions, creams, foams, patches, suspensions, solutions, and suppositories (rectal and vaginal).

Oral formulations containing the active compounds of this invention may comprise any conventionally used oral forms, including tablets, capsules, buccal forms, troches, lozenges and oral liquids, suspensions or solutions. Capsules may contain mixtures of the active compound(s) with inert fillers and/or diluents such as the pharmaceutically acceptable starches (e.g. corn, potato or tapioca starch), sugars, artificial sweetening agents, powdered celluloses, such as crystalline and microcrystalline celluloses, flours, gelatins, gums, etc. Useful tablet formulations may be made by conventional compression, wet granulation or dry granulation methods and utilize pharmaceutically acceptable diluents, binding agents, lubricants, disintegrants, suspending or stabilizing agents, including, but not limited to, magnesium stearate, stearic acid, talc, sodium lauryl sulfate, microcrystalline cellulose, carboxymethylcellulose calcium, polyvinylpyrrolidone, gelatin, alginic acid, acacia gum, xanthan gum, sodium citrate, complex silicates, calcium carbonate, glycine, dextrin, sucrose, sorbitol, dicalcium phosphate, calcium sulfate, lactose, kaolin, mannitol, sodium chloride, talc, dry starches and powdered sugar. Oral formulations herein may utilize standard delay or time release formulations to alter the absorption of the active compound(s). Suppository formulations may be made from traditional materials, including cocoa butter, with or without the addition of waxes to alter the suppository's melting point, and glycerin. Water soluble suppository bases, such as polyethylene glycols of various molecular weights, may also be used.

It is understood that the dosage, regimen and mode of administration of these compounds will vary according to the malady and the individual being treated and will be subject to the judgment of the medical practitioner involved. It is preferred that the administration of one or more of the compounds herein begin at a low dose and be increased until the desired effects are achieved.

The following procedures describe the preparation of representative examples of this invention.

EXAMPLE 1

6-[(2-Butyl-benzofuran-3-yl)-hydroxy-methyl-naphthalen-2-ol n-Butyllithium (17.9 mL) was added dropwise into a cold (−78° C.) mixture of 6-bromo-2-naphthol (5.0 g, 22.42 mmol), and tetrahydrofuran (100 mL). The reaction mixture was stirred for 2 hours, and then 2-butyl-benzofuran-3-carboxaldehyde (4.53 g, 22.42 mmol), in tetrahydrofuran (5 mL) was added dropwise. The mixture was stirred for 30 minutes, quenched with aqueous ammonium chloride, poured into water, acidified with HCl (2 N), and extracted with ethyl ether. The organic extracts were dried over $MgSO_4$. Evaporation and purification by flash chromatography on silica gel (hexanes/EtOAcc 3:1) gave a yellow solid (6.8 g,): mp 38–40° C.; MS m/e 346 ($M^+$);

Analysis for: $C_{23}H_{22}O_3$ Calc'd: C, 79.74; H, 6.40 Found: C, 80.47; H, 6.30

EXAMPLE 2

6-[(2-Butyl-benzofuran-3-ylmethyl)-naphthalen-2-ol

Triethylsilane (7.4 mL, 46.38 minol) was added into a cold (0° C.) mixture of 6[(2-butyl-benzofuran-3-yl)-hydroxy-methyl-naphthalen-2-ol (8.0 g, 23.19 mmol), and dichloromethane (100 mL). After 10 minutes, trifluoroacetic acid (10 mL) was added into the reaction mixture, and the new mixture was stirred for 30 minutes, poured into water, and extracted with ethyl ether. The organic extracts were dried over $MgSO_4$. Evaporation gave a brown oil (6.2 g): MS m/e 330 ($M^+$);

Analysis for: $C_{23}H_{22}O_2$ Calc'd: C, 83.60; H, 6.71 Found: C, 83.91; H, 6.64

EXAMPLE 3

1-Bromo-6-(2-butyl-benzofuran-3-ylmethyl)-naphthalen-2-ol

Bromine (0.96 mL, 18.78 mmol) in acetic acid (10 mL) was added dropwise over a 30 minutes period into a cold (5° C.) mixture of 6-[(2-butyl-benzofuran-3-ylmethyl)-naphthalen-2-ol (6.2 g, 18.78 mmol), and acetic acid (50 mL). After the addition the mixture was poured into water, and extracted with ethyl ether. The organic extracts were washed with aqueous sodium bisulfite and dried over $MgSO_4$. Evaporation gave a brown oil (5.6 g): 54–56° C. MS m/e 408 (M⁺);

Analysis for: $C_{23}H_{21}BrO_2$ Calc'd: C, 67.49; H, 5.17 Found: C, 67.95; H, 5.05

EXAMPLE 4
[1-Bromo-6-(2-butyl-benzofuran-3-ylmethyl)-naphthalen-2-yloxy]-acetic acid Sodium hydride (0.1 g, 2.68 mmol) was added into a mixture of 1-bromo-6-(2-butyl-benzofuran-3-ylmethyl)-naphthalen-2-ol (1.0 g, 2.44 mmol), and N,N-dimethylformamide (8 mL). The mixture was stirred for 1 hour and then methyl bromoacetate (0.25 L, 2.68 mmol) was added dropwise. The mixture was stirred for 1 hour, poured into water, acidified with HCl (2 N) and extracted with ethyl ether. Evaporation gave a yellow oil (1.15 g). The residue was taken in methyl alcohol (20 mL) and tetrahydrofuran (20 mL) and treated with sodium hydroxide (5 mL). After 30 minutes the mixture was poured into water, acidified with HCl (2 N), and extracted with ethyl ether. Evaporation and purification by flash chromatography on acidic silica gel (hexanes/EtOAc 3:1) gave a white solid (0.81 g,): mp 122–124° C.; MS m/e 466 (M⁺);

Analysis for: $C_{25}H_{23}BrO_4$ Calc'd: C, 64.25; H, 4.96 Found: C, 64.06; H, 4.73

EXAMPLE 5
2-[1-Bromo-6-(2-butyl-benzofuran-3-ylmethyl)-naphthalen-2-yloxy]-3-phenylpropionic acid Diisopropyl azodicarboxylate (0.72 mL, 3.66 mmol) in benzene (5 mL) was added dropwise into a cold (0° C.) mixture of 1-bromo-6-(2-butyl-benzofuran-3-ylmethyl)-naphthalen-2-ol (1.0 g, 2.44 mmol), 3-phenyllactic acid methyl ester (0.66 g, 3.66 mmol), triphenylphosphine (0.96 g, 3.66 mmol), and benzene (20 mL). The reaction mixture was stirred at room temperature for 30 minutes, poured into water, and extracted with ethyl ether. The organic extracts were dried over $MgSO_4$. Evaporation and purification by flash chromatography on silica gel (hexanes/ EtOAc 4:1) gave a yellow oil (1.2 g). The residue was taken in methyl alcohol (20 mL) and tetrahydrofuran (20 mL) and treated with sodium hydroxide (5 mL). After 30 minutes the mixture was poured into water, acidified with HCl (2 N), and extracted with ethyl ether. Evaporation and purification by flash chromatography on acidic silica gel (hexanes/EtOAc 3:1) gave a white solid (0.91 g,): mp 98–100° C.; MS m/e 556 (M⁺);

Analysis for: $C_{32}H_{29}BrO_4$ Calc'd: C, 69.94; H, 5.24 Found: C, 68.56; H, 5.31

EXAMPLE 6
5-[1-Bromo-6-(2-butyl-benzofuran-3-ylmethyl)-naphthalen-2-yloxymethyl]-1H-tetrazole Sodium hydride (0.16 g, 3.96 mmol) was added into a mixture of 1-bromo-6-(2-butyl-benzofuran-3-ylmethyl)-naphthalen-2-ol (1.35 g, 3.3 mmol), and N,N-dimethylformamide (10 mL). The mixture was stirred for 1 hour and then bromoacetonitrile (0.27 mL, 3.96 mmol) was added dropwise. The mixture was stirred for 1 hour, poured into water, acidified with HCl (2 N) and extracted with ethyl ether. Evaporation gave a yellow oil (1.15 g). The residue was taken in N,N-dimethylformamide (20 mL) and treated with sodium azide (1.29, 19.8 mmol), and ammonium chloride (1.05 g, 19.8 inmol). The mixture was stirred at 120° C. for 10 hours, poured into water, acidified with HCl (2 N) and extracted with ethyl ether. The organic extracts were dried over MgSO4. Evaporation and purification by flash chromatography on acidic silica gel (hexanes/EtOAc 2:1) gave a white solid (0.98 g): mp 148–150° C.; MS m/e 490 (M⁺);

Analysis for: $C_{25}H_{23}BrN_4O_2$ Calc'd: C, 61.11; H, 4.72; N, 11.40 Found: C, 61.06; H, 4.62; N, 11.46

EXAMPLE 7
6-(2-Butyl-benzofuran-3-ylmethyl)-1-iodo-naphthalen-2-ol

Iodine (1.16 g, 4.55 mmol) was added portionwise into a cold (0° C.) mixture of 6-[(2-butyl-benzofuran-3-ylmethyl)-naphthalen-2-ol (1.5 g, 4.55 mmol), sodium hydroxide (0.35 g, 9.1 mmol) and methyl alcohol (20 mL). The reaction mixture was stirred for 3 hours, poured into water, acidified with HCl (2 N) and extracted with ethyl acetate. The organic extracts were dried over MgSO4. Evaporation and purification by flash chromatography on silica gel (hexanes/EtOAc 2:1) gave a brown oil (1.85 g): MS m/e 476 (M⁺);

Analysis for: $C_{23}H_{21}IO_2$ Calc'd: C, 60.54; H, 4.64; N, 11.40 Found: C, 60.39; H, 4.79; N, 11.46

EXAMPLE 8
2-r-6-(2-Butyl-benzofuran-3-ylmethyl)-1-iodo-naphthalen-2-yloxy]-3-phenyl-propionic acid The title compound was prepared from 6-(2-butyl-benzofuran-3-ylmethyl)-1-iodo-naphthalen-2-ol, and 3-phenyllactic acid, in substantially the same manner, as described in Example 5, and was obtained as a white solid, mp 116–118° C.; MS m/e 604 (M⁺);

Analysis for: $C_{32}H_{29}IO_4$ Calc'd: C, 63.58; H, 4.84 Found: C, 63.41; H, 4.55

EXAMPLE 9
1-Bromo-6-[(2-butyl-benzofuran-3-yl)-hydroxy-methyl]-naphthalen-2-ol Sodium borohydride (0.33 g, 8.98 mmol) was added into a mixture of 1-bromo-6-(2-butyl-benzofuran-3-carbonyl)-naphthalen-2-ol (1.9 g, 4.49 mmol) and methyl alcohol (10 mL). The reaction mixture was stirred for 1 hour poured into water, acidified with HCl (2 N) and extracted with ethyl ether. The organic extracts were dried over MgSO4. Evaporation and purification by flash chromatography on silica gel (hexanes/EtOAc 2:1) gave an off-white solid(1.65 g): MS m/e 424 (M⁺);

Analysis for: $C_{23}H_{21}BrO_3$ Calc'd: C, 64.95; H, 4.98 Found: C, 64.56; H, 4.93

EXAMPLE 10
[1-Bromo-6-(2-butyl-benzofuran-3-carbonyl)-naphthalen-2-yloxy]-acetic acid The title compound was prepared from 1-bromo-6-(2-butyl-benzofuran-3-carbonyl)-naphthalen-2-ol, and methyl bromoacetate, in substantially the same manner, as described in Example 4, and was obtained as a white solid, mp 163–165° C.; MS m/e 680 (M⁺);

Analysis for: $C_{25}H_{21}BrO_5$ Calc'd: C, 62.38; H, 4.40 Found: C, 62.01; H, 4.13

EXAMPLE 11
2-[1-Bromo-6-(2-butyl-benzofuran-3-carbonyl)-naphthalen-2-yloxy]-3-phenylpropionic acid The title compound was prepared from 1-bromo-6-(2-butyl-benzofuran-3-carbonyl)-naphthalen-2-ol, and 3-phenyllactic methyl ester, in substantially the same manner, as described in Example 5, and was obtained as a white solid, mp 165–167° C.; MS m/e 570 (M⁺);

Analysis for: $C_{32}H_{27}BrO_5$ Calc'd: C, 67.25; H, 4.76 Found: C, 67.32; H, 4.59

EXAMPLE 12

[5-bromo-6-(1H-tetrazol-5-ylmethoxy)-naphthalen-2-yl]-(2-butyl-benzofuran-3-yl)methanone The title compound was prepared from 1-bromo-6-(2-butyl-benzofuran-3-carbonyl)-naphthalen-2-ol, in substantially the same manner, as described in Example 6, and was obtained as a white solid, mp 160–162° C.; MS m/e 504 (M+);

Analysis for: $C_{25}H_{21}BrN_4O_3$ Calc'd: C, 59.42; H, 4.19; N, 11.09 Found: C, 59.46; H, 3.92; N, 11.09

EXAMPLE 13

6-(2-Benzyl-benzo[b]thiophen-3-ylmethyl)-1-bromo-naphthalen-2-ol

The title compound was prepared 2-benzyl-benzo[b]thiophene, in substantially the same manner, as described in Examples 1–3, and was obtained as an off-white solid, mp 110–112° C.; MS m/e 458 (M+);

Analysis for: $C_{26}H_{19}BrOS$ Calc'd: C, 67.98; H, 4.17 Found: C, 67.76; H, 4.01

EXAMPLE 14

4'-[(2-Butyl-benzofuran-3-yl)-hydroxy-methyl]-biphenyl-4-ol

The title compound was prepared from 2-butylbenzofuran-3-carboxaldehyde, and 4'-(4-bromophenyl)-phenol, in substantially the same manner, as described in Example 1, and was obtained as a yellow solid, mp 47–49° C.; MS m/e 372 (M+);

Analysis for: $C_{25}H_{24}O_3$ Calc'd: C 80.62; H, 6.50 Found: C, 80.22; H, 6.59

EXAMPLE 15

(2-Butyl-benzofuran-3-yl)-(4'-hydroxy-biphenyl-4-yl)-methanone

Pyridinium chlorochromate (1.74 g, 8.06 mmol), was added into a mixture of 4'-[(2-butyl-benzofuran-3-yl)-hydroxy-methyl]-biphenyl-4-ol (2.0 g, 5.37 mmol), and dichloromethane (20 mL). The reaction mixture was stirred for 1 hour, diluted with ethyl ether and filtered through a florisil pad. The organic extracts were dried over MgSO4. Evaporation and purification by flash chromatography on silica gel (hexanes/EtOAc 3:1) gave a yellow solid(1.1 g): MS m/e 370 (M+);

Analysis for: $C_{25}H_{22}O_3$ Calc'd: C, 81.06; H, 5.99 Found: C, 79.99; H, 5.69

EXAMPLE 16

4'-[(2-Butyl-benzofuran-3-ylmethyl]-biphenyl-4-ol

The title compound was prepared from of 4'-[(2-butyl-benzofuran-3-yl)hydroxy-methyl]-biphenyl-4-ol, in substantially the same manner, as described in Example 2, and was obtained as an off-white solid, mp 104–106° C.; MS m/e 356 (M+);

Analysis for: $C_{25}H_{24}O_2$ Calc'd: C 84.24; H, 6.79 Found: C, 83.65; H, 6.78

EXAMPLE 17

[4'-[(2-Butyl-benzofaran-3-ylmethyl]-biphenyl-4-yloxyl]-acetic acid

The title compound was prepared from 4'-[(2-butyl-benzofuran-3-ylmethyl]biphenyl-4-ol, and methyl bromoacetate in substantially the same manner, as described in Example 4, and was obtained as a white solid, mp 138–140° C.; MS m/e 414 (M+);

Analysis for: $C_{27}H_{26}O_4$ Calc'd: C 78.24; H, 6.32 Found: C, 77.80; H, 6.29

EXAMPLE 18

[4'-(2-Butyl-benzofuran-3-yl)-hydroxy-methyl-biphenyl-4-yloxymethyl]-1H-tetrazole The title compound was prepared from 4'-[(2-butyl-benzofuran-3-ylmethyl]biphenyl-4-ol, and bromo acetonitrile in substantially the same manner, as described in Example 6, and was obtained as a white solid, mp 166–168° C.; MS m/e 438 (M+);

Analysis for: $C_{27}H_{26}N_4O_2$ Calc'd: C 73.95; H, 5.98; N, 12.78 Found: C, 73.75; H, 5.80; N, 12.92

EXAMPLE 19

{4'-[(2-Butyl-benzofuran-3-yl)-hydroxy-methyl]-biphenyl-4-yloxy}-acetic acid

The title compound was prepared from 4'-[(2-butyl-benzofuran-3-yl)-hydroxymethyl]-biphenyl-4-ol, and methyl bromoacetate in substantially the same manner, as described in Example 4, and was obtained as a yellow solid, mp 111–113° C.; MS m/e 430 (M+);

Analysis for: $C_{27}H_{26}OS$ Calc'd: C 75.33; H, 6.08 Found: C, 75.48; H, 6.28

EXAMPLE 20

3,5-Dibromo-4'-[(2-butyl-benzofuran-3-yl)-hydroxy-methyl]-biphenyl-4-ol

The title compound was prepared from 4'-(4-bromophenyl)-2,6-dibromophenol, and 2-butyl benzofuran-3-carboxaldehyde in substantially the same manner, as described in Example 1, and was obtained as a yellow solid, mp 60–62° C.; MS m/e 528 (M+);

Analysis for: $C_{25}H_{22}Br_2O_3$ Calc'd: C 56.63; H, 4.18 Found: C, 57.00; H, 4.10 Example 21

4'-[(2-Benzyl-benzorblthiophen-3-yl)-hydroxy-methyl]-biphenyl-4-ol

The title compound was prepared from 4'-(4-bromophenyl)-phenol, and 2-benzyl benzo[b[thiophen-3-carboxaldehyde in substantially the same manner, as described in Example 1, and was obtained as a white solid, mp 103–105° C.; MS m/e 422 (M+);

Analysis for: $C_{28}H_{22}O_2S \times 0.4 H_2O$ Calc'd: C, 78.26; H, 5.35 Found: C, 78.33; H, 5.10

EXAMPLE 22

(2-Butyl-benzofuran-3-yl)-[5-(4-methoxy-phenyl)-oxazole-2-yl]-methanol

The title compound was prepared from 2-(4-methoxy-phenyl)-oxazole, and 2-butyl benzofuran-3-carboxaldehyde in substantially the same manner, as described in Example 1, and was obtained as a yellow oil; MS m/e 377 (M+);

Analysis for: $C_{23}H_{23}NO_4$ Calc'd: C 73.19; H, 6.14; N, 3.71 Found: C, 72.48; H, 6.11; N, 3.61

EXAMPLE 23

(2-Butyl-benzofuran-3-yl)-[5-(4-methoxy-phenyl)-oxazole-2-yl]-methanone

The title compound was prepared from (2-butyl-benzofuran-3-yl)-[5-(4-methoxy-phenyl)-oxazole-2-yl]-methanol in substantially the same manner, as described in Example 15, and was obtained as a yellow oil; MS m/e 375 (M+);

Analysis for: $C_{23}H_{21}NO_4$ Calc'd: C 73.58; H, 5.64; N, 3.73 Found: C, 73.19; H, 5.33; N, 3.70

EXAMPLE 24

2-(2-Butyl-benzofuran-3-ymethyl)-5-(4-methoxy-phenyl)-oxazole

The title compound was prepared from (2-butyl-benzofuran-3-yl)-[5-(4-methoxy-phenyl)-oxazole-2-yl]- methanol in substantially the same manner, as described in Example 2, and was obtained as a white solid, mp 87–89° C.; MS m/e 361 (M+);
Analysis for: $C_{23}H_{23}NO_3$ Calc'd: C 73.64; H, 6.41; N, 3.88 Found: C, 76.25; H, 6.23; N, 3.93

EXAMPLE 25

[4-Bromo-5-(4-methoxy-phenyl)-oxazol-2-yl]-(2-butyl-benzofuran-3-yl)-methanone

The title compound was prepared from (2-butyl-benzofuran-3-yl)-[5-(4-methoxy-phenyl)-oxazole-2-yl]-methanone in substantially the same manner, as described in Example 3, and was obtained as a yellow solid, mp 62–64° C.; MS m/e 454 (M+);
Analysis for: $C_{23}H_2BrNO_4$ Calc'd: C 60.81; H, 4.44; N, 3.08 Found: C, 60.04; H, 4.12; N, 3.03

EXAMPLE 26

4-Bromo-5-(6-bromo-2-butyl-benzofuran-3-ylmethyl)-5-(4-methoxy-phenyl)-oxazole

The title compound was prepared from 2-(2-butyl-benzofuran-3-ymethyll)-5-(4-methoxy-phenyl)-oxazole in substantially the same manner, as described in Example 3, and was obtained as a yellow solid, mp 93–95° C.; MS m/e 517 (M+);
Analysis for: $C_{23}H_{21}Br_2NO_3$ Calc'd: C 53.20; H, 4.08; N, 2.70 Found: C, 53.27; H, 4.07; N, 2.80

EXAMPLE 27

6-[(Benzothiazol-2-ylsulfanyl)-(2-butyl-benzofuran-3-yl)-methyl-naphthalen-2-ol

Tributylphosphine (0.79 mL, 3.19 mmol) was added dropwise into a mixture of 6-[(2-butyl-benzofuran-3-ylmethyl)-naphthalen-2-ol (1.0 g, 2.9 mmol), 2,2'-dithiobis (benzothiazole) (1.06 g, 3.19 mmol) and toluene (20 mL). The reaction mixture was refluxed for 9 hours poured into water, and extracted with ethyl ether. The organic extracts were dried over MgSO4. Evaporation and purification by flash chromatography on silica gel (hexanes/EtOAc 3:1) gave a white solid(0.95 g): MS m/e 495 (M+);
Analysis for: $C_{30}H_{25}NO_2S_2$ Calc'd: C, 72.70; H, 5.08; N, 2.83 Found: C, 72.52; H, 5.01; N, 2.78

EXAMPLE 28

4'-[(2-Butyl-benzofuran-3-yl)-(benzothiazol-2-ylsulfanyl)-methyl]-biphenyl-4-ol

The title compound was prepared from 4'-[(2-butyl-benzofuran-3-yl)-hydroxymethyl]-biphenyl-4-ol in substantially the same manner, as described in Example 27, and was obtained as a white solid, mp 130–132° C.; MS m/e 521 (M+);
Analysis for: $C_{32}H_{29}NO_2S_2$ Calc'd: C 73.39; H, 5.58; N, 2.67 Found: C, 73.12; H, 5.19; N, 2.69

EXAMPLE 29

2-[1-(Benzorblthiophen-2-yl)-octylsulfanyl]-benzothiazole

The title compound was prepared from (2-octyl-benzo[b] thiophene)-2-hydroxyl in substantially the same manner, as described in Example 27, and was obtained as a yellow oil, MS m/e 411 (M+);
Analysis for: $C_{23}H_{25}NS_3$ Calc'd: C 67.11; H, 6.12; N, 3.40 Found: C, 67.45; H, 6.11; N, 3.43

EXAMPLE 30

2-[(4-Bromo-phenyl)-(2-butyl-benzofuran-3-yl)-methylsulfanyl]-benzothiazole

The title compound was prepared from (2-butyl-benzofuran-3-yl)-hydroxymethyl]-4-bromo-benzene in substantially the same manner, as described in Example 27, and was obtained as a clear oil, MS m/e 508 (M+);
Analysis for: $C_{26}H_{22}BrNOS_2$ Calc'd: C 61.41; H, 4.36; N, 2.75 Found: C, 61.57; H, 4.31; N, 2.72

EXAMPLE 31

2-[(4-Bromo-naphthalen-1-yl)-(2-butyl-benzofuran-3-yl)-methylsulfanyl]-benzothiazole The title compound was prepared from (2-butyl-benzofuran-3-yl)-hydroxymethyl]4-bromo-naphthalene in substantially the same manner, as described in Example 27, and was obtained as a white solid, mp 56–58 MS; m/e 557 (M+);
Analysis for: $C_{30}H_{24}BrNOS_2$ Calc'd: C 64.51; H, 4.33; N, 2.51 Found: C, 65.19; H, 4.28; N, 2.60

EXAMPLE 32

2-[(2-Butyl-benzofaran-3-yl-phenyl-methylsulfanyl]-benzothiazole

The title compound was prepared from (2-butyl-benzofuran-3-yl)-hydroxymethyl]-4-benzene in substantially the same manner, as described in Example 27, and was obtained as a light yellow oi, MS m/e 429 (M+);
Analysis for: $C_{26}H_{23}NOS_2$ Calc'd: C 72.69; H, 45.40; N, 3.26 Found: C, 72.56; H, 5.35; N, 3.30

EXAMPLE 33

[2,6-Dibromo-4-(naphthalene-2-carbonyl)-phenoxy]-acetic acid

The title compound was from prepared (naphthalen-2-yl)-[4-(2,6-dibromophenyl-2-ol)]-methanone in substantially the same manner, as described in Example 4, and was obtained as an off-white solid, mp 188–189° C.; MS m/e 461 (M+);
Analysis for: $C_{19}H_{12}Br_2O_4$ Calc'd: C 49.17; H, 2.61 Found: C, 49.08; H, 2.43

EXAMPLE 34

5-[2,6-Dibromo-4-(naphthalen-2-ylmethyl)-phenoxymethyl]-1H-tetrazole

The title compound was from prepared 2,6-dibromo-4-(naphthalen-2-ylmethyl)phenol in substantially the same manner, as described in Example 4, and was obtained as an off-white solid, mp 183–184° C.; MS m/e 471 (M+);
Analysis for: $C_{19}H_{14}Br_2N_4O$ Calc'd: C 48.13; H, 2.98; N, 11.82 Found: C, 47.95; H, 2.81; N, 11.77

What is claimed is:

1. A compound of formula I having the structure

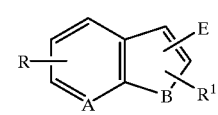

wherein
A is C;
B is O, or S;
E is

or —X—D;
D is

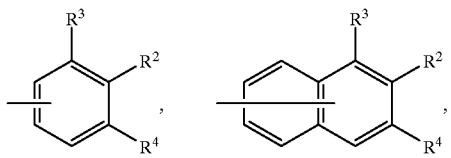

or alkyl of 1–12 carbon atoms;
X is CO, CH(OH), CH₂, or —CH—S-2-benzothiazole;
Y is hydrogen, alkyl of 1–6 carbon atoms, or halogen;
Z is O, S, or N;
R is hydrogen, alkyl of 1–6 carbon atoms, alkoxy of 1–6 carbon atoms, halogen, or trifluoromethyl;
$R^1$ is alkyl of 1–12 carbon atoms, aryl of 6–10 carbon atoms, aralkyl of 7–15 carbon atoms, halogen, Het-alkyl wherein the alkyl moiety contains 1–6 carbon atoms, or aryl mono-, di- or tri-substituted with a substituent selected from the group consisting of halogen, alkyl of 1–6 carbon atoms, trifluoromethyl, and alkoxy of 1–6 carbon atoms;
Het is

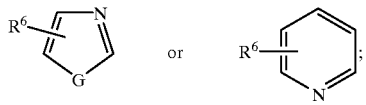

G is O, S, or N;
$R^2$ is hydrogen, halogen, alkyl of 1–6 carbon atoms, or —$OR^5$
$R^3$ and $R^4$ are each, independently, hydrogen, halogen, alkyl of 1–8 carbon atoms, aryl of 6–12 carbon atoms, nitro, amino, alkylsulfoamide, arylsulfoamide, cycloalkyl of 3–8 carbon atoms, heterocycle of 5 to 7 ring atom containing from 1 to 3 heteroatoms selected from oxygen, nitrogen, or sulfur, or aryl of 6–10 carbon atoms mono-, di- or tri-substituted with a substituent selected from the group consisting of halogen, alkyl of 1–6 carbon atoms, trifluoromethyl, alkoxy of 1–6 carbon atoms;
$R^5$ is hydrogen, alkyl of 1–6 carbon atoms, —$CH(R^7)R^8$, —$C(CH_2)_nCO_2R^9$, —$C(CH_3)_2CO_2R^9$, $CH(R^7)(CH_2)_nCO_2R^9$, or —$CH(R^7)C_6H_4CO_2R^9$;
$R^6$ is alkylene of 1–3 carbon atoms;
$R^7$ is hydrogen, alkyl of 1–6 carbon atoms, aryl of 6–12 carbon atoms, aralkyl of 6–12 carbon atoms, cycloalkyl of 3–8 carbon atoms, phthalic acid, or Q-alkyl wherein the alkyl moiety contains 1–6 carbon atoms;
Q is

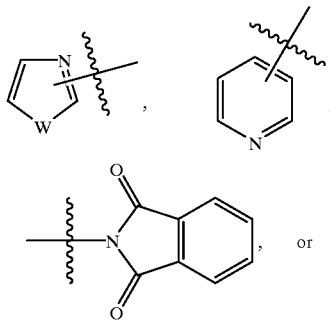

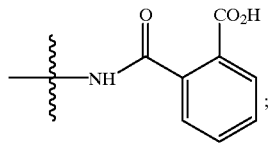

$R^8$ is —$CO_2R^{11}$, —$CONHR^{11}$, tetrazole, or —$PO_3R^{11}$;
$R^9$ is hydrogen, alkyl of 1–6 carbon atoms, aryl of 6–12 carbon atoms, or aralkyl of 7–15 carbon atoms;
W is O, N, or S;
$R^{11}$ is hydrogen, alkyl of 1–6 carbon atoms, aryl of 6–12 carbon atoms, or aralkyl of 7–15 carbon atoms;
n=1–6;
or a pharmaceutically acceptable salt thereof with the proviso that when E is —X—D, D is not

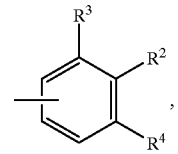

further provided that when E is X— D, R1 cannot be phenyl substituted with alkoxy.

2. The compound according to claim 1, wherein
A is C;
R is hydrogen;
$R^1$ is hydrogen, alkyl of 1–6 carbon atoms, or aralkyl of 7–15 carbon atoms; and
$R^3$ and $R^4$ are each, independently, hydrogen or halogen;
or a pharmaceutically acceptable salt thereof.

3. The compound according to claim 1 which is 6-[(2-butyl-benzofuran-3-yl)hydroxy-methyl-naphthalen-2-ol or a pharmaceutically acceptable salt thereof.

4. The compound according to claim 1 which is 6-[(2-butyl-benzofuran-3-ylmethyl)-naphthalen-2-ol or a pharmaceutically acceptable salt thereof.

5. The compound according to claim 1 which is 1-bromo-6-(2-butyl-benzofuran-3-ylmethyl)-naphthalen-2-ol or a pharmaceutically acceptable salt thereof.

6. The compound according to claim 1 which is [1-bromo-6-(2-butyl-benzofuran-3-ylmethyl)-naphthalen-2-yloxy]-acetic acid or a pharmaceutically acceptable salt thereof.

7. The compound according to claim 1 which is 2-[1-bromo-6-(2-butyl-benzofuran-3-ylmethyl)-naphthalen-2-yloxy]-3-phenyl-propionic acid or a pharmaceutically acceptable salt thereof.

8. The compound according to claim 1 which is 5-[1-bromo-6-(2-butyl-benzofuran-3-ylmethyl)-naphthalen-2-yloxymethyl]-1H-tetrazole or a pharmaceutically acceptable salt thereof.

9. The compound according to claim 1 which is 6-(2-butyl-benzofuran-3-ylmethyl)-1-iodo-naphthalen-2-ol or a pharmaceutically acceptable salt thereof.

10. The compound according to claim 1 which is 2-[-6-(2-butyl-benzofuran-3-ylmethyl)-1-iodo-naphthalen-2-yloxy]-3-phenyl-propionic acid or a pharmaceutically acceptable salt thereof.

11. The compound according to claim 1 which is 1-bromo-6-[(2-butyl-benzofaran-3-yl)-hydroxy-methyl]-naphthalen-2-ol or a pharmaceutically acceptable salt thereof.

12. The compound according to claim 1 which is [1-bromo-6-(2-butyl-benzofuran-3-carbonyl)-naphthalen-2-yloxy]-acetic acid or a pharmaceutically acceptable salt thereof.

13. The compound according to claim 1 which is 2-[1-bromo-6-(2-butyl-benzofuran-3-carbonyl)-naphthalen-2-yloxy]-3-phenyl-propionic acid or a pharmaceutically acceptable salt thereof.

14. The compound according to claim 1 which is [5-bromo-6-(1H-tetrazol-5-ylmethoxy)-naphthalen-2-yl]-(2-butyl-benzofuran-3-yl)-methanone or a pharmaceutically acceptable salt thereof.

15. The compound according to claim 1 which is 6-(2-benzyl-benzo[b]thiophen-3-ylmethyl)-1-bromo-naphthalen-2-ol or a pharmaceutically acceptable salt thereof.

16. The compound according to claim 1 which is 4'-[(2-butyl-benzofuran-3-yl)hydroxy-methyl]-biphenyl-4-ol or a pharmaceutically acceptable salt thereof.

17. The compound according to claim 1 which is (2-butyl-benzofuran-3-yl)-(4'-hydroxy-biphenyl-4-yl)-methanone or a pharmaceutically acceptable salt thereof.

18. The compound according to claim 1 which is 4'-[(2-butyl-benzofuran-3-ylmethyl]-biphenyl-4-ol or a pharmaceutically acceptable salt thereof.

19. The compound according to claim 1 which is [4'-[(2-butyl-benzofuran-3-ylmethyl]-biphenyl-4-yloxy]-acetic acid or a pharmaceutically acceptable salt thereof.

20. The compound according to claim 1 which is 5-[4'-(2-butyl-benzofuran-3-ylmethyl)-biphenyl-4-yloxymethyl]-1H-tetrazole or a pharmaceutically acceptable salt thereof.

21. The compound according to claim 1 which is {4'-[(2-butyl-benzofuran-3-yl)hydroxy-methyl]-biphenyl-4-yloxy}-acetic acid or a pharmaceutically acceptable salt thereof.

22. The compound according to claim 1 which is 3,5-dibromo-4'-[(2-butylbenzofuran-3-yl)-hydroxy-methyl]-biphenyl-4-ol or a pharmaceutically acceptable salt thereof.

23. The compound according to claim 1 which is 4'-[(2-benzyl-benzorb]thiophen-3-yl)-hydroxy-methyl]-biphenyl-4-ol or a pharmaceutically acceptable salt thereof.

24. The compound according to claim 1 which is (2-butyl-benzofuran-3-yl)-[5-(4-methoxy-phenyl)-oxazole-2-yl]-methanol or a pharmaceutically acceptable salt thereof.

25. The compound according to claim 1 which is (2-butyl-benzofuran-3-yl)-[5-(4-methoxy-phenyl)-oxazol-2-yl]-methanone or a pharmaceutically acceptable salt thereof.

26. The compound according to claim 1 which is 2-(2-butyl-benzofuran-3-ymethyl)-5-(4-methoxy-phenyl)-oxazol or a pharmaceutically acceptable salt thereof.

27. The compound according to claim 1 which is [4-bromo-5-(4-methoxy-phenyl)oxazol-2-yl]-(2-butyl-benzofuran-3-yl)-methanone or a pharmaceutically acceptable salt thereof.

28. The compound according to claim 1 which is 4-bromo-5-(6-bromo-2-butylbenzofuran-3-ylmethyl)-5-(4-methoxy-phenyl)-oxazole or a pharmaceutically acceptable salt thereof.

29. The compound according to claim 1 which is 6-[(benzothiazol-2-ylsulfanyl)-(2-butyl-benzofuran-3-yl)-methyl]-naphthalen-2-ol or a pharmaceutically acceptable salt thereof.

30. The compound according to claim 1 which is 4'-[(2-butyl-benzofuran-3-yl)(benzothiazol-2-ylsulfanyl)-methyl]-biphenyl-4-ol or a pharmaceutically acceptable salt thereof.

31. The compound according to claim 1 which is 2-[1-(benzo[b]thiophen-2-yl)octylsulfanyl]-benzothiazole or a pharmaceutically acceptable salt thereof.

32. The compound according to claim 1 which is 2-[(4-bromo-phenyl)-(2-butylbenzofuran-3-yl)-methylsulfanyl]-benzothiazole or a pharmaceutically acceptable salt thereof.

33. The compound according to claim 1 which is 2-[(4-bromo-naphthalen-1-yl)-(2-butyl-benzofuran-3-yl)-methylsulfanyl]-benzothiazole or a pharmaceutically acceptable salt thereof.

34. The compound according to claim 1 which is 2-[(2-butyl-benzofuran-3-yl)phenyl-methylsulfanyl]-benzothiazole or a pharmaceutically acceptable salt thereof.

35. A method of treating metabolic disorders mediated by insulin resistance or hyperglycemia in a mammal in need thereof which comprises administering to said mammal, a compound of formula I having the structure

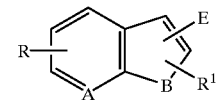

I wherein
A is C;
B is O, or S;
E is

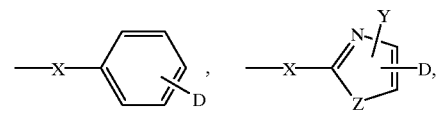

or —X—D;
D is

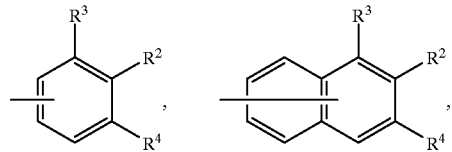

or alkyl of 1–12 carbon atoms;
X is CO, CH(OH), CH2, or —CH—S-2-benzothiazole;
Y is hydrogen, alkyl of 1–6 carbon atoms, or halogen;
Z is O, S, or N;
R is hydrogen, alkyl of 1–6 carbon atoms, alkoxy of 1–6 carbon atoms, halogen, or trifluoromethyl;
$R^1$ is alkyl of 1–12 carbon atoms, aryl of 6–10 carbon atoms, aralkyl of 7–15 carbon atoms, halogen, Het-alkyl wherein the alkyl moiety contains 1–6 carbon atoms, or aryl mono-, di- or tri-substituted with a substituent selected from the group consisting of halogen, alkyl of 1–6 carbon atoms, trifluoromethyl, and alkoxy of 1–6 carbon atoms;
Het is

G is O, S, or N;
$R^2$ is hydrogen, halogen, alkyl of 1–6 carbon atoms, or —$OR^5$
$R^3$ and $R^4$ are each, independently, hydrogen, halogen, alkyl of 1–8 carbon atoms, aryl of 6–12 carbon atoms, nitro, amino, alkylsulfoamide, arylsulfoamide, cycloalkyl of 3–8 carbon atoms, heterocycle of 5 to 7 ring atom containing from 1 to 3 heteroatoms selected from oxygen, nitrogen, or sulfur, or aryl of 6–10 carbon atoms mono-, di- or tri-substituted with a substituent selected from the group consisting of halogen, alkyl of 1–6 carbon atoms, trifluoromethyl, alkoxy of 1–6 carbon atoms;

$R^5$ is hydrogen, alkyl of 1–6 carbon atoms, —CH($R^7$)$R^8$, —C(CH$_2$)$_n$CO$_2$R$^9$, —C(CH$_3$)$_2$CO$_2$R$^9$, CH($R^7$)(CH$_2$)$_n$CO$_2$R$^9$, or —CH($R^7$)C$_6$H$_4$CO$_2$R$^9$;

$R^6$ is alkylene of 1–3 carbon atoms;

$R^7$ is hydrogen, alkyl of 1–6 carbon atoms, aryl of 6–12 carbon atoms, aralkyl of 6–12 carbon atoms, cycloalkyl of 3–8 carbon atoms, phthalic acid, or Q-alkyl wherein the alkyl moiety contains 1–6 carbon atoms;

Q is

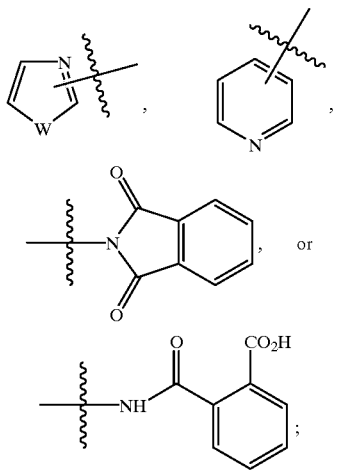

$R^8$ is —CO$_2$R$^{11}$, —CONHR$^{11}$, tetrazole, or —PO$_3$R$^{11}$;

$R^9$ is hydrogen, alkyl of 1–6 carbon atoms, aryl of 6–12 carbon atoms, or aralkyl of 7–15 carbon atoms;

W is O, N, or S;

$R^{11}$ is hydrogen, alkyl of 1–6 carbon atoms, aryl of 6–12 carbon atoms, or aralkyl of 7–15 carbon atoms;

n=1–6;

or a pharmaceutically acceptable salt thereof.

36. A method of treating or inhibiting type II diabetes in a mammal in need thereof which comprises administering to said mammal, a compound of formula I having the structure

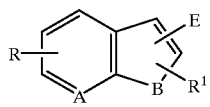    I wherein

A is C;

B is O, or S;

E is

or —X—D;

D is

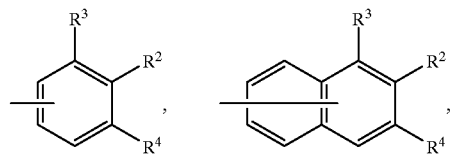

or alkyl of 1–12 carbon atoms;

X is CO, CH(OH), CH$_2$, or —CH—S-2-benzothiazole;

Y is hydrogen, alkyl of 1–6 carbon atoms, or halogen;

Z is O, S, or N;

R is hydrogen, alkyl of 1–6 carbon atoms, alkoxy of 1–6 carbon atoms, halogen, or trifluoromethyl;

$R^1$ is alkyl of 1–12 carbon atoms, aryl of 6–10 carbon atoms, aralkyl of 7–15 carbon atoms, halogen, Het-alkyl wherein the alkyl moiety contains 1–6 carbon atoms, or aryl mono-, di- or tri-substituted with a substituent selected from the group consisting of halogen, alkyl of 1–6 carbon atoms, trifluoromethyl, and alkoxy of 1–6 carbon atoms;

Het is

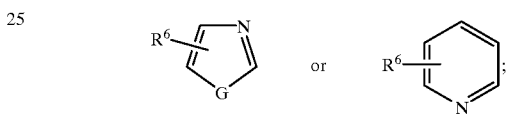

G is O, S, or N;

$R^2$ is hydrogen, halogen, alkyl of 1–6 carbon atoms, or —OR$^5$ $R^3$ and $R^4$ are each, independently, hydrogen, halogen, alkyl of 1–8 carbon atoms, aryl of 6–12 carbon atoms, nitro, amino, alkylsulfoamide, arylsulfoamide, cycloalkyl of 3–8 carbon atoms, heterocycle of 5 to 7 ring atom containing from 1 to 3 heteroatoms selected from oxygen, nitrogen, or sulfur, or aryl of 6–10 carbon atoms mono-, di- or tri-substituted with a substituent selected from the group consisting of halogen, alkyl of 1–6 carbon atoms, trifluoromethyl, alkoxy of 1–6 carbon atoms;

$R^5$ is hydrogen, alkyl of 1–6 carbon atoms, —CH($R^7$)$R^8$, —C(CH$_2$)$_n$CO$_2$R$^9$, —C(CH$_3$)$_2$CO$_2$R$^9$, CH($R^7$)(CH$_2$), CO$_2$R$^9$, or —CH($R^7$)C$_6$H$_4$CO$_2$R$^9$;

$R^6$ is alkylene of 1–3 carbon atoms;

$R^7$ is hydrogen, alkyl of 1–6 carbon atoms, aryl of 6–12 carbon atoms, aralkyl of 6–12 carbon atoms, cycloalkyl of 3–8 carbon atoms, phthalic acid, or Q-alkyl wherein the alkyl moiety contains 1–6 carbon atoms;

Q is

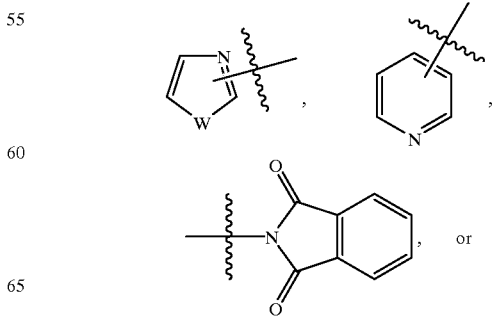

-continued

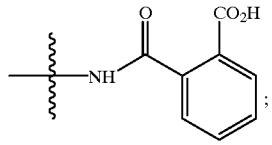

$R^8$ is —$CO_2R^{11}$, —$CONHR^{11}$, tetrazole, or —$PO_3R^{11}$;
$R^9$ is hydrogen, alkyl of 1–6 carbon atoms, aryl of 6–12 carbon atoms, or aralkyl of 7–15 carbon atoms;
W is O, N, or S;
$R^{11}$ is hydrogen, alkyl of 1–6 carbon atoms, aryl of 6–12 carbon atoms, or aralkyl of 7–15 carbon atoms;
n=1–6;

or a pharmaceutically acceptable salt thereof.

37. A method of modulating glucose levels in a mammal in need thereof which comprises administering to said mammal, a compound of formula I having the structure

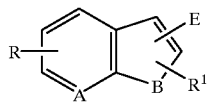

I wherein

A is C;
B is O, or S;
E is

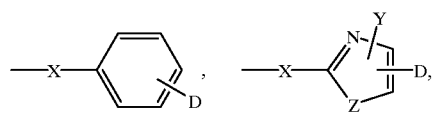

or —X—D;

D is

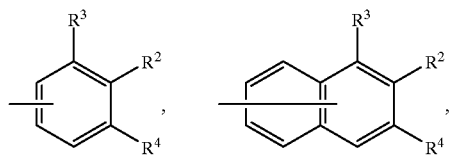

or alkyl of 1–12 carbon atoms;

X is CO, CH(OH), $CH_2$, or —CH—S-2-benzothiazole;
Y is hydrogen, alkyl of 1–6 carbon atoms, or halogen;
Z is O, S, or N;
R is hydrogen, alkyl of 1–6 carbon atoms, alkoxy of 1–6 carbon atoms, halogen, or trifluoromethyl;
$R^1$ is alkyl of 1–12 carbon atoms, aryl of 6–10 carbon atoms, aralkyl of 7–15 carbon atoms, halogen, Het-alkyl wherein the alkyl moiety contains 1–6 carbon atoms, or aryl mono-, di- or tri-substituted with a substituent selected from the group consisting of halogen, alkyl of 1–6 carbon atoms, trifluoromethyl, and alkoxy of 1–6 carbon atoms;

Het is

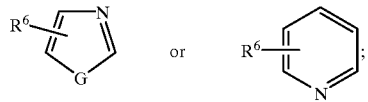

G is O, S, or N;
$R^2$ is hydrogen, halogen, alkyl of 1–6 carbon atoms, or —$OR^5$
$R^3$ and $R^4$ are each, independently, hydrogen, halogen, alkyl of 1–8 carbon atoms, aryl of 6–12 carbon atoms, nitro, amino, alkylsulfoamide, arylsulfoamide, cycloalkyl of 3–8 carbon atoms, heterocycle of 5 to 7 ring atom containing from 1 to 3 heteroatoms selected from oxygen, nitrogen, or sulfur, or aryl of 6–10 carbon atoms mono-, di- or tri-substituted with a substituent selected from the group consisting of halogen, alkyl of 1–6 carbon atoms, trifluoromethyl, alkoxy of 1–6 carbon atoms;
$R^5$ is hydrogen, alkyl of 1–6 carbon atoms, —$CH(R^7)R^8$, —$C(CH_2)_nCO_2R^9$, —$C(CH_3)_2CO_2R^9$, $CH(R^7)(CH_2)_nCO_2R^9$, or —$CH(R^7)C_6H_4CO_2R^9$;
$R^6$ is alkylene of 1–3 carbon atoms;
$R^7$ is hydrogen, alkyl of 1–6 carbon atoms, aryl of 6–12 carbon atoms, aralkyl of 6–12 carbon atoms, cycloalkyl of 3–8 carbon atoms, phthalic acid, or Q-alkyl wherein the alkyl moiety contains 1–6 carbon atoms;

Q is

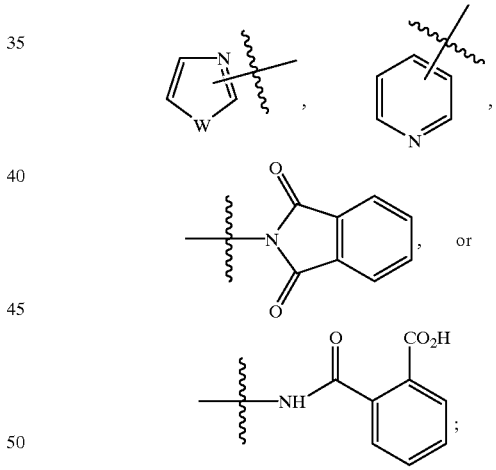

$R^8$ is —$CO_2R^{11}$, —$CONHR^{11}$, tetrazole, or —$PO_3R^{11}$;
$R^9$ is hydrogen, alkyl of 1–6 carbon atoms, aryl of 6–12 carbon atoms, or aralkyl of 7–15 carbon atoms;
W is O, N, or S;
$R^{11}$ is hydrogen, alkyl of 1–6 carbon atoms, aryl of 6–12 carbon atoms, or aralkyl of 7–15 carbon atoms;
n=1–6;

or a pharmaceutically acceptable salt thereof.

38. A pharmaceutical composition which comprises a compound of formula I having the structure

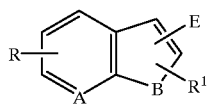

wherein
A is C;
B is O, or S;
E is

or —X—D;
D is

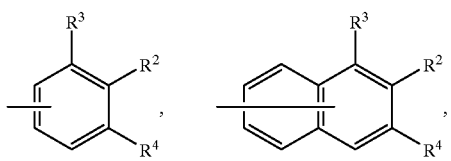

or alkyl of 1–12 carbon atoms;
X is CO, CH(OH), CH$_2$, or —CH—S-2-benzothiazole;
Y is hydrogen, alkyl of 1–6 carbon atoms, or halogen;
Z is O, S, or N;
R is hydrogen, alkyl of 1–6 carbon atoms, alkoxy of 1–6 carbon atoms, halogen, or trifluoromethyl;
R$^1$ is alkyl of 1–12 carbon atoms, aryl of 6–10 carbon atoms, aralkyl of 7–15 carbon atoms, halogen, Het-alkyl wherein the alkyl moiety contains 1–6 carbon atoms, or aryl mono-, di- or tri-substituted with a substituent selected from the group consisting of halogen, alkyl of 1–6 carbon atoms, trifluoromethyl, and alkoxy of 1–6 carbon atoms;
Het is

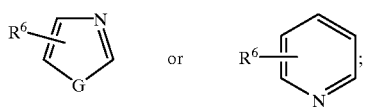

G is O, S, or N;
R$^2$ is hydrogen, halogen, alkyl of 1–6 carbon atoms, or —OR$^5$
R$^3$ and R$^4$ are each, independently, hydrogen, halogen, alkyl of 1–8 carbon atoms, aryl of 6–12 carbon atoms, nitro, amino, alkylsulfoamide, arylsulfoamide, cycloalkyl of 3–8 carbon atoms, heterocycle of 5 to 7 ring atom containing from 1 to 3 heteroatoms selected from oxygen, nitrogen, or sulfur, or aryl of 6–10 carbon atoms mono-, di- or tri-substituted with a substituent selected from the group consisting of halogen, alkyl of 1–6 carbon atoms, trifluoromethyl, alkoxy of 1–6 carbon atoms;
R$^5$ is hydrogen, alkyl of 1–6 carbon atoms, —CH(R$^7$)R$^8$, —C(CH$_2$)$_n$CO$_2$R$^9$, —C(CH$_3$)$_2$CO$_2$R$^9$, CH(R$^7$)(CH$_2$)$_n$CO$_2$R$^9$, or —CH(R$^7$)C$_6$H$_4$CO$_2$R$^9$;
R$^6$ is alkylene of 1–3 carbon atoms;
R$^7$ is hydrogen, alkyl of 1–6 carbon atoms, aryl of 6–12 carbon atoms, aralkyl of 6–12 carbon atoms, cycloalkyl of 3–8 carbon atoms, phthalic acid, or Q-alkyl wherein the alkyl moiety contains 1–6 carbon atoms;
Q is

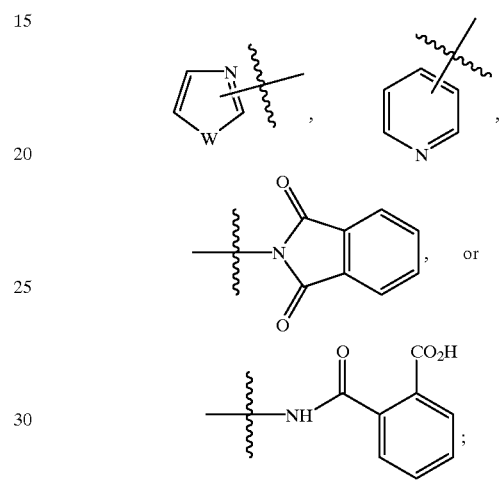

R$^8$ is —CO$_2$R$^{11}$, —CONHR$^{11}$, tetrazole, or —PO$_3$R$^{11}$;
R$^9$ is hydrogen, alkyl of 1–6 carbon atoms, aryl of 6–12 carbon atoms, or aralkyl of 7–15 carbon atoms;
W is O, N, or S;
R$^{11}$ is hydrogen, alkyl of 1–6 carbon atoms, aryl of 6–12 carbon atoms, or aralkyl of 7–15 carbon atoms;
n=1–6;
or a pharmaceutically acceptable salt thereof with the proviso that when E is —X—D, D is not

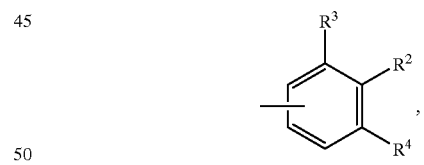

, further provided that when E is X— D, R1 cannot be phenyl substituted with alkoxy and a pharmaceutical carrier.

* * * * *